US008574259B2

(12) United States Patent
Welch et al.

(10) Patent No.: US 8,574,259 B2

(45) Date of Patent: Nov. 5, 2013

(54) INTRAVASCULAR FILTER WITH DRUG RESERVOIR

(75) Inventors: Eric D. Welch, Miramar, FL (US); Timothy S. Girton, Edina, MN (US); Joel M. WasDyke, Eden Prairie, MN (US)

(73) Assignee: Lifescreen Sciences LLC, Frisco, TX (US)

( * ) Notice: Subject to any disclaimer, the term of this patent is extended or adjusted under 35 U.S.C. 154(b) by 1867 days.

(21) Appl. No.: 11/125,531

(22) Filed: May 10, 2005

(65) Prior Publication Data

US 2006/0259067 A1 Nov. 16, 2006

(51) Int. Cl.
*A61M 29/00* (2006.01)

(52) U.S. Cl.
USPC .......... 606/200

(58) Field of Classification Search
USPC .......... 606/200
See application file for complete search history.

(56) References Cited

U.S. PATENT DOCUMENTS 3,334,629 A 8/1967 Cohn
3,467,102 A 9/1969 Fogarty et al.
3,540,431 A 11/1970 Mobin-Uddin
3,868,956 A 3/1975 Alfidi et al.
3,952,747 A 4/1976 Kimmell, Jr.
4,391,797 A 7/1983 Folkman et al.
4,425,908 A 1/1984 Simon
4,430,081 A 2/1984 Timmermans
4,459,317 A 7/1984 Lambert
4,487,808 A 12/1984 Lambert
4,494,531 A 1/1985 Gianturco
4,619,246 A 10/1986 Molgaard-Nielsen et al.
4,643,184 A 2/1987 Mobin-Uddin
4,650,466 A 3/1987 Luther
4,662,885 A 5/1987 DiPisa, Jr.
4,675,361 A 6/1987 Ward, Jr.
4,688,553 A 8/1987 Metals
4,727,873 A 3/1988 Mobin-Uddin
4,781,177 A 11/1988 Lebigot
4,793,348 A 12/1988 Palmaz
4,817,600 A 4/1989 Herms et al.
4,832,055 A 5/1989 Palestrant
4,873,978 A 10/1989 Ginsburg
4,925,698 A 5/1990 Klausner et al.
4,943,460 A 7/1990 Markle et al.
4,957,501 A 9/1990 Lahille et al.
4,959,074 A 9/1990 Halpern et al.
4,969,891 A 11/1990 Gewertz
4,980,231 A 12/1990 Baker et al.

(Continued)

FOREIGN PATENT DOCUMENTS

EP 0 117 940 A2 9/1984
EP 0 270432 A1 6/1988

(Continued)

*Primary Examiner* — Darwin Erezo
*Assistant Examiner* — Jing Ou
(74) *Attorney, Agent, or Firm* — Seager, Tufte & Wickhem LLC

(57) ABSTRACT

An intravascular filter can capture and eliminate emboli. In particular, an intravascular filter may include a plurality of filter legs extending from an apical head. The filter legs may be configured to capture emboli. A drug reservoir that includes or contains a therapeutic drug can be disposed near the apical head. The therapeutic drug, such as a thrombolytic or anti-coagulatory drug, may be eluted in response to a captured emboli.

11 Claims, 5 Drawing Sheets

10
22
12
16
14
20
18

(56) References Cited

U.S. PATENT DOCUMENTS 4,990,156 A 2/1991 Lefebvre
4,998,539 A 3/1991 Delsanti
5,002,582 A 3/1991 Guire et al.
5,026,607 A 6/1991 Kiezulas
5,035,706 A 7/1991 Giantureo et al.
5,037,656 A 8/1991 Pitt et al.
5,037,677 A 8/1991 Halpern et al.
5,059,205 A 10/1991 El-Nounou et al.
5,071,407 A 12/1991 Termin et al.
5,102,402 A 4/1992 Dror et al.
5,108,418 A 4/1992 Lefebvre
5,108,419 A 4/1992 Reger et al.
5,133,733 A 7/1992 Rasmussen et al.
5,135,516 A 8/1992 Sahatjian et al.
5,147,379 A 9/1992 Sabbaghian et al.
5,152,777 A 10/1992 Goldberg et al.
5,160,342 A 11/1992 Reger et al.
5,160,790 A 11/1992 Elton
5,234,458 A 8/1993 Metais
5,242,462 A 9/1993 El-Nounou et al.
5,250,613 A 10/1993 Bergstrom et al.
5,304,121 A 4/1994 Sahatjian
5,324,304 A 6/1994 Rasmussen
5,330,768 A 7/1994 Park et al.
5,370,657 A 12/1994 Irie
5,380,299 A 1/1995 Fearnot et al.
5,383,928 A 1/1995 Scott et al.
5,419,760 A 5/1995 Narciso, Jr.
5,443,458 A 8/1995 Eury
5,447,724 A 9/1995 Helmus et al.
5,449,382 A 9/1995 Dayton
5,451,428 A 9/1995 Rupp
5,464,650 A 11/1995 Berg et al.
5,512,055 A 4/1996 Domb et al.
5,545,208 A 8/1996 Wolff et al.
5,562,922 A 10/1996 Lambert
5,578,075 A 11/1996 Dayton
5,591,227 A 1/1997 Dinh et al.
5,601,595 A 2/1997 Smith
5,605,696 A 2/1997 Eury et al.
5,616,608 A 4/1997 Kinsella et al.
5,624,411 A 4/1997 Tuch
5,626,605 A 5/1997 Irie et al.
5,626,862 A 5/1997 Brem et al.
5,669,933 A 9/1997 Simon et al.
5,674,192 A 10/1997 Sahatjian et al.
5,679,400 A 10/1997 Tuch
5,702,754 A 12/1997 Zhong
5,704,910 A * 1/1998 Humes .......................... 604/502
5,709,704 A 1/1998 Nott et al.
5,716,981 A 2/1998 Hunter et al.
5,722,984 A 3/1998 Fischell et al.
5,733,925 A 3/1998 Kunz et al.
5,776,184 A 7/1998 Tuch
5,800,525 A 9/1998 Bachinski et al.
5,837,008 A 11/1998 Berg et al.
5,837,313 A 11/1998 Ding et al.
5,911,704 A * 6/1999 Humes ....................... 604/93.01
6,156,373 A 12/2000 Zhong et al.
6,214,025 B1 4/2001 Thistle et al.
6,273,901 B1 8/2001 Whitcher et al.
6,468,290 B1 * 10/2002 Weldon et al. ................ 606/200
6,589,266 B2 7/2003 Whitcher et al.
6,602,271 B2 * 8/2003 Adams et al. ................. 606/200
6,716,208 B2 * 4/2004 Humes ....................... 604/891.1
6,746,469 B2 * 6/2004 Mouw ........................... 606/200
2001/0001817 A1 * 5/2001 Humes ....................... 604/892.1
2002/0090389 A1 * 7/2002 Humes et al. ................. 424/422
2002/0161390 A1 * 10/2002 Mouw ........................... 606/200
2002/0193828 A1 * 12/2002 Griffin et al. ................. 606/200
2003/0004539 A1 * 1/2003 Linder et al. .................. 606/200
2003/0065346 A1 * 4/2003 Evens et al. ................... 606/153
2003/0153943 A1 * 8/2003 Michael et al. ............... 606/200
2003/0171771 A1 * 9/2003 Anderson et al. ............. 606/200
2003/0235602 A1 12/2003 Schwarz
2004/0073252 A1 * 4/2004 Goldberg et al. ............. 606/200
2004/0158274 A1 * 8/2004 WasDyke ...................... 606/200

FOREIGN PATENT DOCUMENTS

EP 0 293 605 A1 12/1988
EP 0 350 043 A1 1/1990
EP 0 430 848 A1 6/1991
EP 0 472 334 A1 2/1992
EP 1 486 182 A2 12/2004
FR 2 570 288 A1 3/1986
FR 2 573 646 A1 5/1986
FR 2 580 504 A1 10/1986
WO WO 92/03097 A1 3/1992
WO WO 93/12723 A1 7/1993
WO WO 97/33552 A1 9/1997
WO 02/056796 A1 7/2002

* cited by examiner

INTRAVASCULAR FILTER WITH DRUG RESERVOIR

TECHNICAL FIELD

The invention relates generally to filters and relates more specifically to filters such as intravascular filters that include a drug reservoir.

BACKGROUND

Intravascular filters can be used to treat vascular conditions such as pulmonary embolism. These devices can be inserted intravenously into a target location of the body such as an artery or vein, and can capture blood clots (emboli) contained in the blood stream before they can reach the heart and/or lungs and cause permanent damage to the body. An intravascular filter can be placed percutaneously via an introducer sheath through the femoral arteries or the jugular vein using a local anesthetic, or by performing a laparotomy with the patient under general anesthesia.

A variety of intravascular filters such as vena cava filters are known. However, a need remains for improved designs. A need remains for intravascular filters having improved ability to dissolve or lyse captured emboli.

SUMMARY

The present invention is directed to an intravascular filter that captures and eliminates emboli.

Accordingly, an illustrative embodiment of the present invention can be found in an intravascular filter that has a plurality of filter legs. Each filter leg has a free end and an opposite joined end. The intravascular filter also has an apical head. The joined end of each of the filter legs is joined to the apical head and each of the filter legs radiate outwardly from the apical head. A drug reservoir that includes or contains a therapeutic drug is disposed near the apical head.

Another illustrative embodiment of the present invention can be found in a method of dissolving embolic debris within a vasculature. An intravascular filter having an apical head and a drug reservoir positioned at or near the apical head is deployed. The drug reservoir includes a thrombolytic drug. The thrombolytic drug is eluted from the drug reservoir in response to an emboli contacting the drug reservoir, thereby dissolving the embolic debris.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
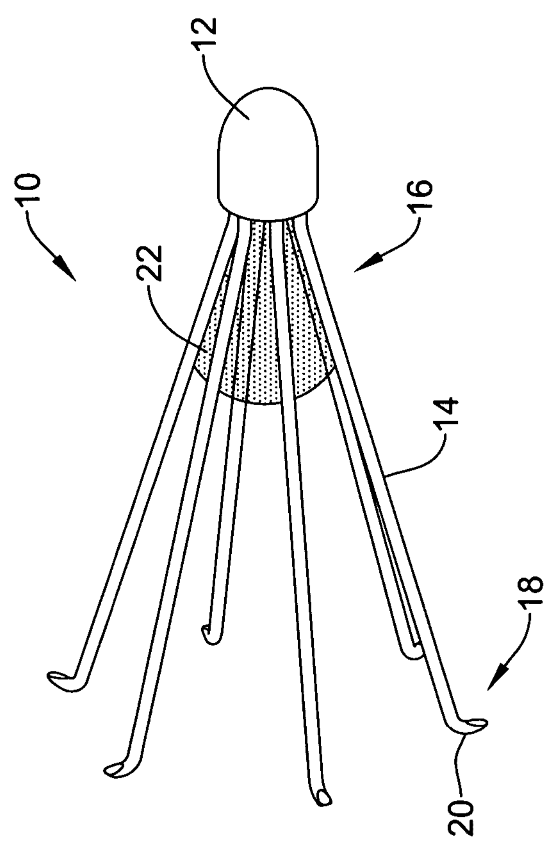
FIG. 1 is a perspective view of an intravascular filter in accordance with an illustrative embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term “about”, whether or not explicitly indicated. The term “about” generally refers to a range of numbers that one of skill in the art would consider equivalent to the recited value, i.e., having the same function or result. In many instances, the term “about” may include numbers that are rounded to the nearest significant figure.

As used in this specification and in the appended claims, the singular forms “a”, “an”, and “the” include plural referents unless the content clearly dictates otherwise. As used in this specification and in the appended claims, the term “or” is generally employed in its sense including “and/or” unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a perspective view of an intravascular filter 10. For illustrative but non-limiting purposes, the present invention will be discussed with respect to vena cava filters. The intravascular filter 10 includes an apical head 12 and several filter legs 14. Each of the filter legs 14 has a joined end 16 and a free end 18. The joined end 16 of each filter leg 14 may be joined to the apical head 12. In some instances, the joined end 16 may be laser welded to the apical head 12, although other attachment methods may be used as appropriate. The intravascular filter 10 may have three, four, five, six, or more filter legs 14. In some cases, the filter legs 14 may be arranged in opposing pairs. In some instances, as illustrated, a hook or barb 20 may be located at the free end 18 of each filter leg 14 to facilitate positioning and securing the intravascular filter 10 in a suitable intra-vascular location.

The intravascular filter 10 can be formed of any suitable material. In some embodiments, it can be useful to form the intravascular filter 10 of a metallic material that permits compression of the intravascular filter 10 into a delivery configuration while allowing the intravascular filter 10 to regain its deployment configuration after the intravascular filter 10 has been deployed. Suitable metals include platinum, gold, tantalum, tungsten, titanium, or stainless steel, and shape memory materials such as nickel-titanium alloys. In particular, the intravascular filter 10 can be formed of nickel-titanium alloys, stainless steel enriched with platinum, MP35N, cobalt-chromium-nickel-molyodenum-iron alloy specified by ASTM F1058 and ISO 5832-7 or other suitable material.

The intravascular filter 10 also includes a drug reservoir 22. As illustrated in FIG. 1, the drug reservoir 22 may be positioned near the apical head 12 at a position that is at least substantially interior to the filter legs 14. In some instances, the drug reservoir 22 may include or contain a therapeutic drug such as a thrombolytic agent and/or an anti-coagulant.

Examples of suitable thrombolytic agents include serine proteases such as reteplase (either r-PA or Retavase), alteplase (t-PA or Activase), urokinase (Abbokinase), prourokinase, anisoylated streptokinase activator complex, and streptokinase. Examples of suitable anti-coagulants include heparin or coumadin.

In some instances, the drug reservoir may be formed from a therapeutic agent that is dispersed within a polymer that is designed to permit elution of the therapeutic agent. Any suitable polymer may be used. In some instances, the polymer may be poly(styrene-b-isobutylene-b-styrene), or SIBS. This material is commercially available from Boston Scientific Corporation under the tradename TRANSLUTE™. This is a hydrophobic elastomeric tri-block copolymer that is based upon 1,3-di(2-methoxy-2-propyl)-5-tert-butylbenzene). SIBS has a number-average molecular weight of about 80,000 to 130,000 grams per mole.

The drug reservoir 22 may be formed in any suitable manner. In some instances, the drug reservoir 22, containing or formed from a therapeutic agent dispersed within a polymer, may be formed in place near the apical head 12 by dipping, spraying or any other suitable technique. In such cases, the drug reservoir 22 may extend outwardly from the interior of the space defined by the filter legs 14 and may in fact at least partially encapsulate the apical head 14. In other cases, a plug or other similar shape containing the therapeutic agent dispersed within the polymer may be independently formed and shaped, and subsequently inserted into position within the intravascular filter 10.

Figure 2:
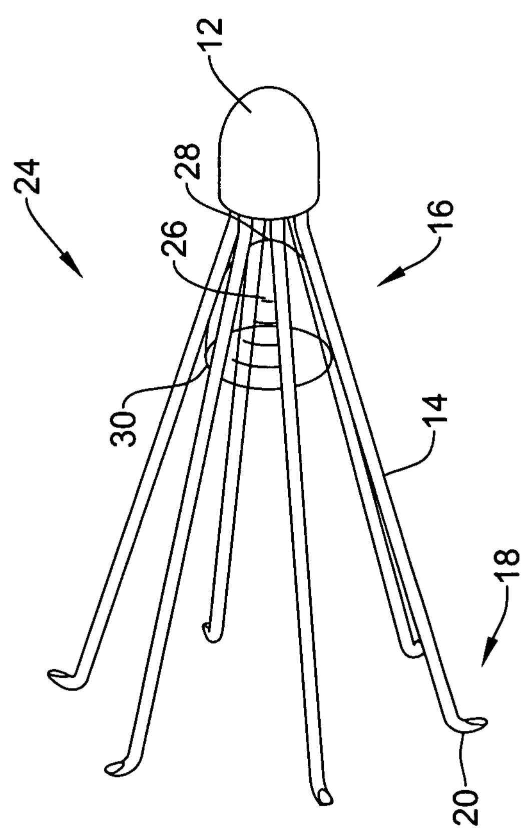
FIG. 2 is a perspective view of an intravascular filter in accordance with another illustrative embodiment of the present invention.

FIG. 2 is a perspective view of an intravascular filter 24 in accordance with another embodiment of the present invention. Construction of the intravascular filter 24 is essentially the same as the intravascular filter 10 discussed with respect to FIG. 1, with the exception of the drug reservoir 26. The intravascular filter 24 includes an apical head 12 and a plurality of filter legs 14. Each filter leg 14 has a joined end 16 and a free end 18 bearing a hook or barb 20. The joined end 16 of each filter leg 14 is secured to the apical head 12.

The intravascular filter 24 differs, however, in the form and construction of the drug reservoir 26. In this embodiment, the drug reservoir 26 takes the form of a bowl or cup having a closed end 28 positioned relatively closer to the apical head 12 and an open end 30 positioned relatively farther from the apical head 12. The drug reservoir 26 may be formed of any suitable material. Examples of suitable materials include plastics and metals such as stainless steel and nitinol. The drug reservoir 26 may be secured to the intravascular filter 24 in any suitable manner, including welding or the use of adhesives.

In use, the intravascular filter 24 would be positioned such that blood would flow from the free end 18 of the filter legs 14 towards the apical head 12. As a result, emboli captured by the intravascular filter 24 will be carried by blood flow towards the apical head 12 and thus will contact the open end 30 of the drug reservoir 26. A therapeutic drug such as those discussed previously with respect to the drug reservoir 22 (FIG. 1) may be eluted or released in response to the emboli contacting the drug reservoir 26.

In some instances, it may be useful to also provide a therapeutic coating onto the filter legs 14 and/or the apical head 12 to further facilitate dissolution of any captured emboli. Any suitable coating may be applied. Examples of suitable coatings include drugs, chemotherapeutics, antibiotics, and the like.

Some examples of appropriate substances may include anti-thrombogenic agents and/or anticoagulants such as heparin, coumadin, heparin derivatives, urokinase, and PPack (dextrophenylalanine proline arginine chloromethylketone) D-Phe-Pro-Arg chloromethyl keton, an RGD peptide-containing compound, antithrombin compounds, platelet receptor antagonists, anti-thrombin antibodies, anti-platelet receptor antibodies, aspirin, prostaglandin inhibitors, platelet inhibitors, and tick antiplatelet peptides; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; anti-sense DNA and RNA; and DNA coding for (and the corresponding proteins) anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's") including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, "hedgehog" proteins.

Figure 3:
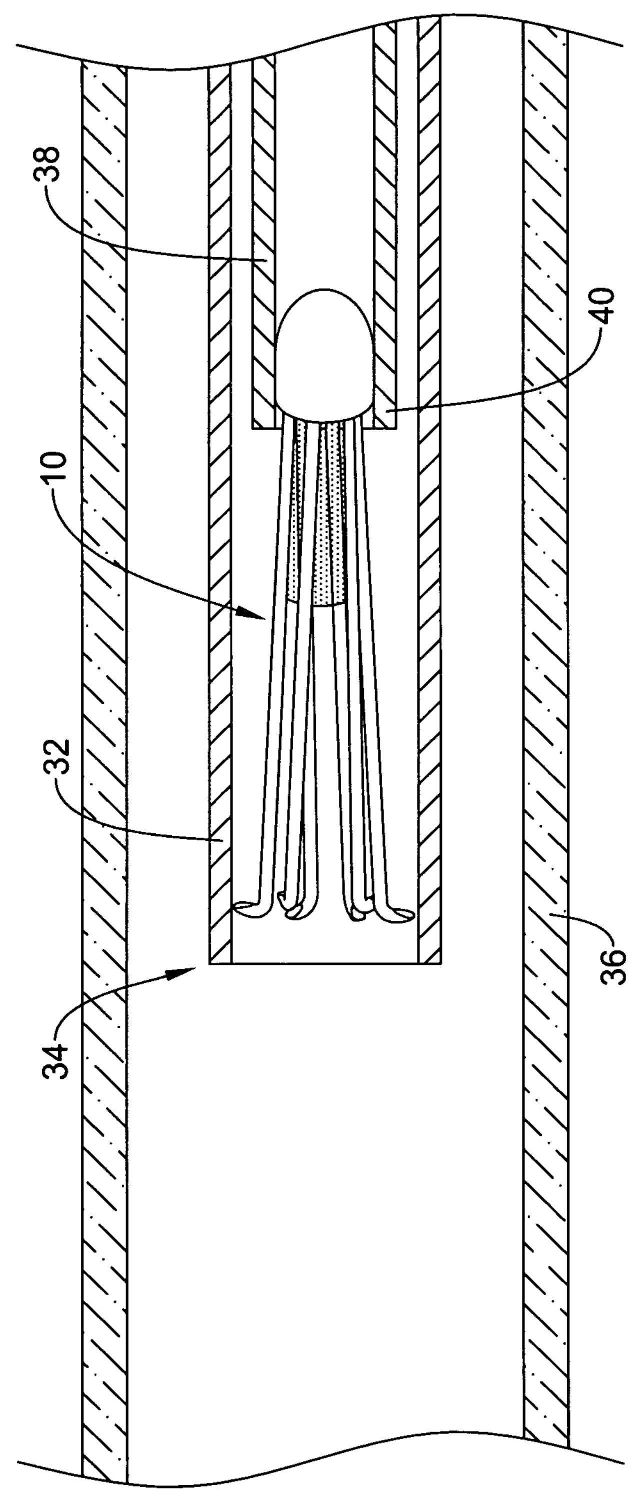
FIG. 3 is a partial cross-sectional view of the intravascular filter of FIG. 1, shown in delivery configuration within an introducer sheath.
Figure 4:
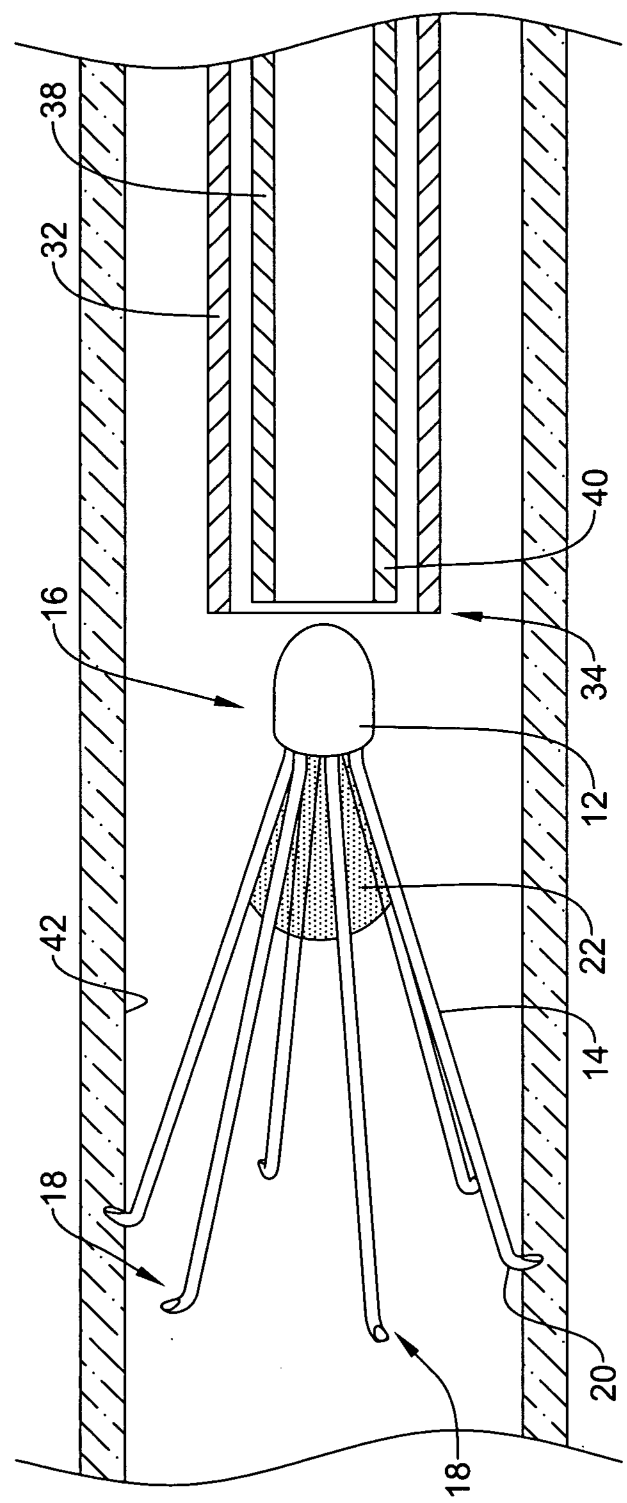
FIG. 4 is a partial cross-sectional view of the intravascular filter of FIG. 1, shown deployed.
Figure 5:
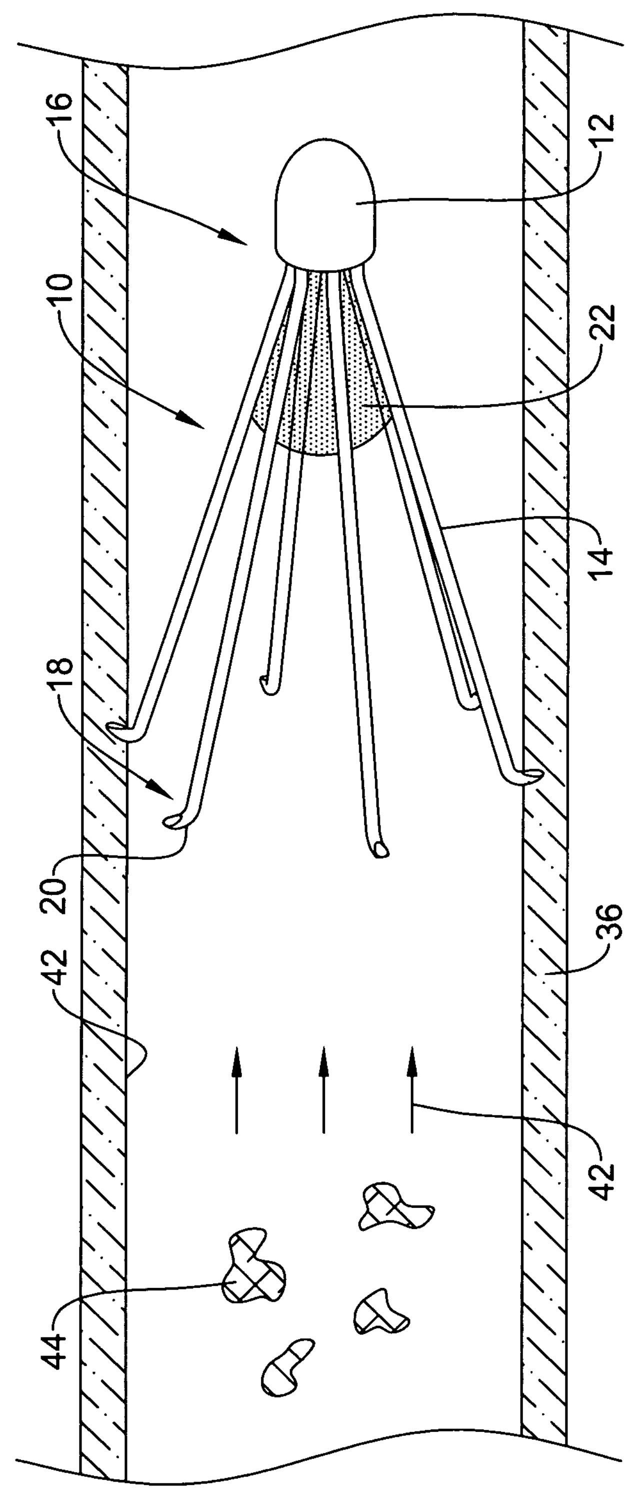
FIG. 5 is a partial cross-sectional view of the intravascular filter of FIG. 1, shown deployed in position to capture emboli.

Returning to the Figures, FIGS. 3-5 illustrate deployment and use of the intravascular filter 10 (FIG. 1), although the intravascular filter 24 (FIG. 2) can be deployed and used in a similar manner. In FIG. 3, the intravascular filter 10 is schematically illustrated in a collapsed or delivery configuration within an introducer sheath 32 having a distal end 34. In some embodiments, the intravascular filter 10 can be delivered to the physician or other healthcare professional preloaded into the introducer sheath 32. In other embodiments, it is considered that the intravascular filter 10 can be loaded into the introducer sheath 32 just prior to insertion of the introducer sheath 32 into a vessel 36. The introducer sheath 32 may be formed of any suitable materials and having any suitable construction, as is known in the art.

The intravascular filter 10 can be moved distally using any conventionally known technique. For example, a pusher sheath 38 having a distal end 40 may be positioned within the introducer sheath 32 and can be used to push against the intravascular filter 10 to urge the intravascular filter 10 distally. It is contemplated that the distal end 40 of the pusher sheath 38 may be configured to accommodate the apical head 12 of the intravascular filter 10. The pusher sheath 38 may be formed of any suitable materials and having any suitable construction, as is known in the art.

In some embodiments, the pusher sheath 38 can hold the intravascular filter 10 while the introducer sheath 32 is withdrawn proximally in order to deploy the intravascular filter 10. In some embodiments, a pressurized fluid such as saline may be used to urge the intravascular filter 10 distally. As the intravascular filter 10 is urged out of the introducer sheath, it transforms into its deployed configuration. FIG. 4 illustrates the intravascular filter 10 in a fully deployed configuration. In FIG. 4, it can be seen that the hooks or barbs 20 that are present at the free ends 19 of the filter legs 14 engage with a vessel wall 42 of the blood vessel 36.

FIG. 5 illustrates the intravascular filter 10 deployed within a patient's vessel 36 in which blood flow is indicated by arrows 42. The apical head 12 and drug reservoir 22 is downstream of an open end of the intravascular filter 10 defined by the free ends 18 of the filter legs 14. An emboli 44 is seen moving towards the intravascular filter 10. As the emboli 44 moves closer, it will be guided by the filter legs 14 towards the center of the intravascular filter 10 and thus towards the drug reservoir 22. The drug reservoir may elute a therapeutic drug, such as those discussed above, in order to facilitate dissolution of the emboli 44.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. An intravascular filter, comprising:

a plurality of filter legs, each of the filter legs having a free end and an opposite joined end;

an apical head, the joined end of each of the filter legs secured to the apical head, each of the filter legs radiating outwardly from the apical head; and a drug reservoir disposed near the apical head, the drug reservoir comprising a drug dispersed only within poly (styrene-b-isobutylene-b-styrene), wherein the drug reservoir comprises a cup having a hollow volume positioned inside the plurality of filter legs, the cup having an open end and a closed end, where the closed end is positioned closest to the apical head while the open end extends away from the apical head.

2. The intravascular filter of claim 1, wherein the therapeutic drug comprises a thrombolytic agent.

3. The intravascular filter of claim 2, wherein the thrombolytic agent comprises a drug selected from the group consisting of reteplase, alteplase, urokinase, prourokinase, anisoylated streptokinase activator complex, and streptokinase.

4. The intravascular filter of claim 1, wherein the therapeutic drug comprises an anti-coagulant.

5. The intravascular filter of claim 4, wherein the anticoagulant comprises one of heparin or coumadin.

6. The intravascular filter of claim 1, wherein the poly (styrene-b-isobutylene-b-styrene) is configured to permit the therapeutic drug to elute from the poly(styrene-b-isobutylene-b-styrene).

7. The intravascular filter of claim 1, wherein the plurality of filter legs comprise stainless steel.

8. The intravascular filter of claim 1, wherein the apical head comprises stainless steel.

9. The intravascular filter of claim 1, wherein the plurality of filter legs comprise nitinol.

10. The intravascular filter of claim 1, wherein the apical head comprises nitinol.

11. A method of dissolving embolic debris within a vasculature, comprising steps of:

providing an intravascular filter having an apical head and a drug reservoir positioned at or near the apical head, the drug reservoir comprising a thrombolytic drug dispersed only within poly(styrene-b-isobutylene-b-styrene), wherein the drug reservoir comprises a cup having a hollow volume positioned inside the plurality of filter legs, the cup having an open end and a closed end, where the closed end is positioned closest to the apical head while the open end extends away from the apical head;

deploying the intravascular filter within the vasculature; and eluting a thrombolytic drug from the drug reservoir in response to an emboli contacting the drug reservoir, thereby dissolving the embolic debris.

* * * * *